United States Patent [19]

Pettit et al.

[11] Patent Number: 4,833,257

[45] Date of Patent: May 23, 1989

[54] COMPOSITIONS OF MATTER AND METHODS OF USING SAME

[75] Inventors: George R. Pettit, Paradise Valley; Cherry L. Herald; Yoshiaki Kamano, both of Tempe, all of Ariz.; John E. Leet, Cheshire, Conn.

[73] Assignee: Arizona Board of Regents, Tempe, Ariz.

[21] Appl. No.: 889,946

[22] Filed: Jul. 28, 1986

[51] Int. Cl.$^4$ .......................................... C07D 493/22
[52] U.S. Cl. .................................... 549/267; 514/450
[58] Field of Search ......................................... 549/267

[56] References Cited

PUBLICATIONS

George R. Pettit et al, J. Am. Chem. Soc. (1984), vol. 106, pp. 6768–6771.

G. R. Pettit et al, Tetrahedron, vol. 41(16) (1985), pp. 985–994.

*Primary Examiner*—Glennon H. Hollrah
*Assistant Examiner*—A. A. Owens
*Attorney, Agent, or Firm*—Richard R. Mybeck

[57] ABSTRACT

New and exceptionally potent antineoplastic agents denominated Bryostatin 9, Bryostatin 10, Bryostatin 11, Bryostatin 12 and Bryostatin 13 have been isolated from the marine animal *Bugula neritina* (Linneaeus) (Bryozoan phylum) and the structures identified. Meaningful antineoplastic activity is found for each.

4 Claims, No Drawings

COMPOSITIONS OF MATTER AND METHODS OF USING SAME

The work described herein was partially funded under Contract NO1-CM-97262 with the Division of Cancer Treatment, NCI, National Institutes of Health DHHS; PHS Grants CA 16049 -07, -08 and -09 awarded by the National Cancer Institute, DHHS.

INTRODUCTION

The present invention relates to the isolation and purification of new bryostatins herein denominated, bryostatins 9, 10, 11, 12 and 13 from marine sources and the discovery that these isolates display substantial cell growth inhibitory and antineoplastic activity against the P388 lymphocytic leukemia and other NCI test systems.

The general chemical structure of the bryostatins of the present invention is:

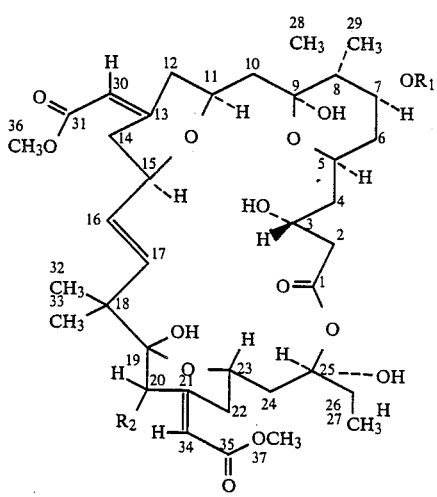

wherein: $R_1 = -COCH_3$; $-COCH_2CH_2CH_3$; or $-COCH_2CH(CH_3)_2$ $R_2 = -H$, $-OCOCH_2$; or $-O-CO(CH)_4(CH_2)_2CH_3$

BACKGROUND OF THE INVENTION

Fossil records suggest many cataclysmic events in evolution of the phylum Bryozoa and a great number of ancient members have become extinct. The 4,000 plus species that presently exist, represent a very competitive group of animals with highly developed survival mechanisms. Perhaps due to their generally pedestrian appearance and likelihood of being mistaken for seaweeds, hydroids or corals, these otherwise fascinating "moss animals" have received little biological and chemical study. Because of our earlier observations that extracts of the marine bryozoan Bugula neritina (Linnaeus) exhibited exceptional antineoplastic activity (100% life extension) against the U.S. National Cancer Institute murine P388 lymphocytic leukemia (PS system), we undertook an extensive investigation of such constituents. Fourteen years later we were able to report the isolation and x-ray crystal structure of bryostatin 1, the first member of what we hope to be a very potent (low dose) class of new antitumor substances. Subsequently, we discovered other bryostatins of the bryostatins 1 and 4 types which were found to possess remarkable (PS inhibition to 10 μg/kg dose levels) antineoplastic activity. In the same period, other bryozoans were found to contain new pyrrole, indole, quinoline, and purine marine alkaloids with some displaying antibacterial, antifungal, or antialgal activity while others inhibited the division of fertilized sea urchin egg cells.

In the continuing effort to locate and define various natural and synthesizable substances for treatment of one or more varieties of cancer, research chemists continue to look at natural flora and fauna in an attempt to isolate and identify new substances which exhibit antineoplastic activity while substantially minimizing, if not totally eliminating, some of the severe side effects accompanying known chemotherapeutic agents.

It is in the further pursuit of these goals that marine species heretofore ignored are now being examined to determine whether they contain constituents which when isolated, will exhibit antineoplastic activity.

Accordingly, a principal object of the present invention is to provide new agents useful in the retardation or remission of one or more types of cancer.

Another object of the present invention is to provide methods and procedures for isolating antineoplastic substances from marine plant life in a form whereby they may be readily and usefully employed in the therapeutic treatment and management of one or more types of cancer which occur in human hosts.

A further object of the present invention is the provision of unique means and methods for isolating and identifying new 20-desoxybryostatins from marine sources.

These and still further objects as shall hereinafter appear are readily fulfilled by the present invention in a remarkably unexpected manner as will be readily discerned from the following detailed description of an exemplary embodiments thereof.

BRIEF SUMMARY OF THE INVENTION

Continual investigation of biologically active Bugula neritina has now led to five new bryostatins herein designated Bryostatins 9, 10, 11, 12 and 13. Bryostatins 10, 11 and 13 represent a new class of bryostatins, termed 20-desoxy-bryostatins. Of these, Bryostatin 9 significantly inhibits (PS $ED_{50} = 1.2 \times 10^{-3}$ μg/ml with 40% life extension at 80 μg/kg) growth of the U.S. National Cancer Institutes P388 lymphocytic leukemia (PS system) as is hereafter reported.

Both Bryostatins 10 and 11 proved to be markedly active against the PS leukemia exhibiting PS cell line growth inhibition at $ED_{50}$ $7.6 \times 10^{-4}$ and $1.8 \times 10^{-5}$ μg/mL and in vivo growth inhibition at, for example, 10 μg/kg and 64% at 92.5 μg/kg respectively, while Bryostatins 12 and 13 also exhibited meaningful activity against the PS leukemia cell line at $ED_{50}$ (0.014 μg/mL with at 47–68% life extension at 30–50 μg/kg for Bryostatin 12; and $ED_{50}$ 0.0054 μg/mL for Bryostatins 13.

DETAILED DESCRIPTION OF THE INVENTION

Description of the Organism

Marine animals of the phylum Ectoprocta (usually termed Bryozoa or Polyzoa) are colonial filter-feeders and each member (polypide) is enclosed in a separate unit (zooecium). Because of their superficial appearance Bryozoa are commonly known as sea-mats and false corals.

Bugula neritina (Linnaeus) is a widely distributed moss-like bryozoan and is well known for its ability to attach to ship hulls.

*B. neritina* and other marine bryozoans are described by J. H. Day in "A Guide to Marine Life on South African Shores," Balkema, A.A., Cape Town, 1974, p. 123; and by P. H. Benson and R. W. Moncreiff in "The Effects of Zinc and pH on Larval Attachment of the Common Fouling Organism, *Bugula neritina*"; Compt. Rend. du Contres. International de la Corrosion Marine et de Salissures. 4th Antibes and Juan-le-Pins, Fr., July 14–18, 1976.

Location of the Organism

The quantities of bryostatins required for structure determination were isolated from 1000 kg (damp wt.) of *Bugula neritina* specimens that were collected from California coastal areas and 50 kg (wet weight) from the Gulf of Mexico (Alligator Harbor, Florida). They were collected below low tidal depths of 0–5 feet. Other locations where these organisms have been collected include Tokyo Bay, Japan (35° N., 140° E.) and sites near Sinaloa, Mexico. Extracts of *B. neritina* from three separate collections all contained antineoplastic activity.

Isolation and Purification of Bryostatins

A variety of methods can be used to isolate and purify the bryostatins from samples of *B. neritina*, including solvent extraction, partition chromatography, silical gel chromatography, liquid-liquid distribution in a Craig apparatus, adsorption on resins and crystallization from solvents.

The isolation and purification methods chosen can be monitored at each step by performing *in-vitro* and/or *in-vivo* antitumor tests as described by R. I. Geran, N. H. Greenberg, M. M. MacDonald, A. M. Schumacher and B. S. Abbot in *Cancer Chemother. Rep.* Part 3, Vol 3: 1–103 (1972); and by Schmidt, J. M.; Pettit, G. R. in *Experientia* 1978, 34: 659–660. Such tests include the determination of the concentration of active material required to inhibit the growth of tumor cells in culture, (e.g. the concentration required to inhibit growth by 50 percent or the E.D.$_{50}$) and of the dose of active material required to prolong the life of mice bearing transplanted tumors. The chemical structures of the bryostatins of the present invention are shown below and the physical characteristics are reported in the pertinent examples. The structures are:

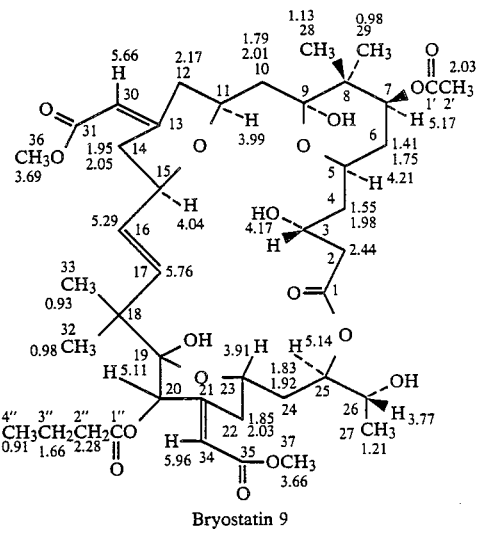

Bryostatin 9

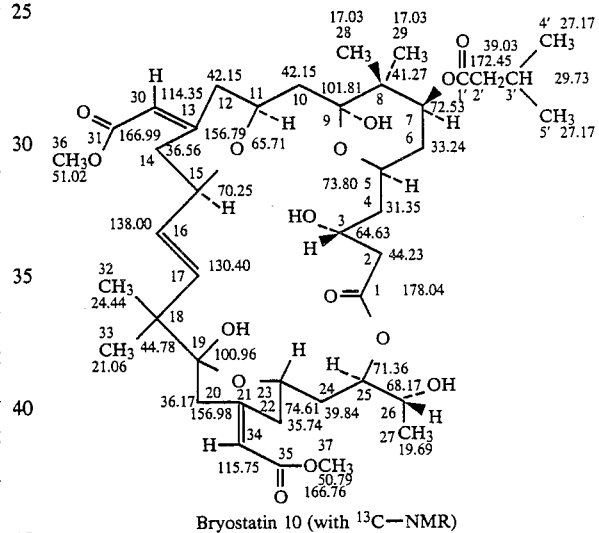

Bryostatin 10 (with $^{13}$C—NMR)

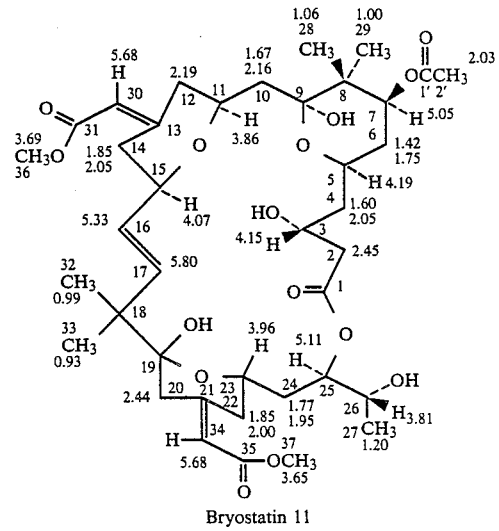

Bryostatin 11

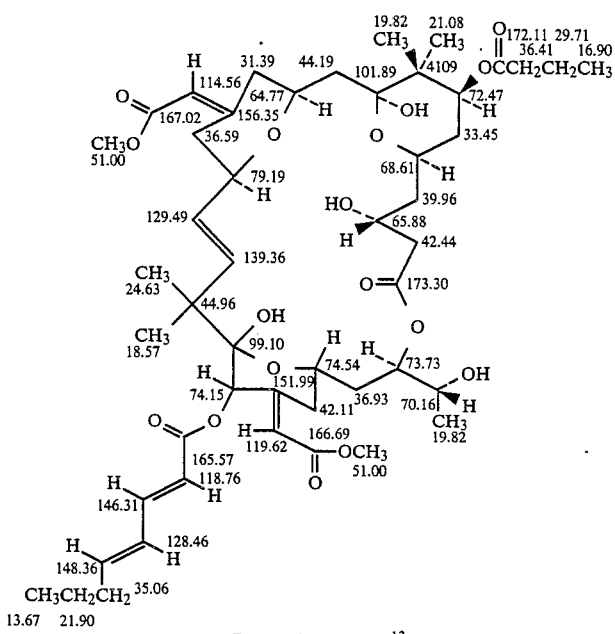

Bryostatin 12 (with $^{13}$C—NMR)

Bryostatin 13 (with $^1$H—NMR)

The bryostatins herein described have free hydroxyl and replaceable acyl groups whereby various acyl esters of the new compounds can be prepared by methods well known in the art. Acyl derivaties of the bryostatins have the same biological ability as the parent compounds.

Acids which can be used in the acylation of Bryostatins 9, 10, 11, 12 and 13 include:

(a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropiolic acid and naphthylacetic acid, and the like. Suitable halo-, nitro-, hydroxy-, keto-, amino-, cyano-, thiocyano-, and lower alkoxyhydrocarbon carboxylic acids include hydrocarboncarboxylic acids as given above which are substituted by one or more of halogen, nitro, hydroxy, keto, amino, cyano, or thiocyano, or lower alkoxy, advantageously lower alkoxy of not more than six carbon atoms, for example, methoxy, ethoxy, propoxy, butoxy, amyloxy, hexyloxy, and isomeric forms thereof. Examples of such substitued hydrocarbon carboxylic acids are: mono-, di-, and trichloroacetic acid; α- and β-chloropropionic acid; α- and α-bromobutyric acid; α- and δ-iodovaleric acid, mevalonic acid; 2- and 4-chlorocyclohexanecarboxylic acid, shikimic acid; 2-nitro-1-methyl-cyclobutanecarboxylic acid; 1, 2, 3, 4, 5, 6-hexachlorocyclohexanecarboxylic acid; 3-bromo-2-methylcyclohexanecarboxylic acid; 4- and 5-bromo-2-methylcyclohexanecarboxylic acid; 5- and 6-bromo-2-methylcyclohexanecarboxylic acid; 2,3-dibromo-2-methylcyclohexanecarboxylic acid; 2,5-dibromo-2-methylcyclohexanecarboxylic acid; 4,5-dibromo-2-methylcyclohexanecarboxylic acid; 5,6-dibromo-2-methylcyclohexanecarboxylic acid; 3-bromo-3-methylcyclohexanecarboxylic acid; 6-bromo-3-methylcyclohexanecarboxylic acid; 1,6-dibromo-3-methylcyclohexanecarboxylic acid; 2-bromo-4-methylcyclocohexanecarboxylic acid; 1,2-dibromo-4-methylcyclohexanecarboxylic acid; 3-bromo-2, 2, 3-trimethylcyclopentanecarboxylic acid; 1-bromo-3,5-dimethylcyclohexanecarboxylic acid; homogentisic acid, o-, m-, and p-chlorobenzoic acid; anisic acid; salicylic acid; p-hydroxybenzoic acid; b-resorcylic acid; gallic acid; veratric acid; trimethoxybenzoic acid; trimethoxycinnamic acid; 4,4'-dichlorobenzilic acid; o-, m-, and p-nitrobenzoic acid; cyanoacetic acid; 3,4- and 3,5-dinitrobenzoic acid; 2,4,6-trinitrobenzoic acid; thiocyanoacetic acid; cyanopropionic acid; lactic acid; ethoxyformic acid (ethyl hydrogen carbonate); malic acid; citric acid; isocitric acid; 6-methylsalicylic acid; mandelic acid; levulinic acid; pyruvic acid; glycine; alamine; valine; isoleucine; leucine; phenylalanine; proline; serine; threonine; tyrosine; hydroxyproline; ornithine; lysine; arginine; histidine; hydroxylysine; phenylglycine; p-aminobenzoic acid; m-aminobenzoic acid; anthranilic acid; aspartic acid; glutamic acid aminoadipic acid; glutamine; asparagine; and the like.

To further aid in the understanding of the present invention but not as a limitation thereupon, reference is made to the following Examples.

EXAMPLE 1

General Procedures. Solvents employed for chromatography were redistilled. Sephadex LH-20 (25–100) used for gel permeation and partition chromatography was obtained from Pharmacia Fine Chemicals, AB, Uppsala, Sweden. Other ambient pressure column chromatographic separations were performed with Silica gel 60 (70–230μ) or Lobar size B Silica 60 (40–63μ) columns supplied by E. Merck (Darmstadt). Gilson UV monitor Model HM and Gilson microfractionators were used for collecting fractions. An HPLC column (10 mm ID×500, Supelco, Inc., Bellefonte, Pa.) packed with Techsil-10M-C-18 reversed phase adsorbent (Phenomenex) prepared by HPLC Technology Ltd., Cheshire, U.K. was used for final purification procedures. The HPLC column was interfaced with an Axxion 710 controller and with two Altex Model 110A pumps. Preparative layer silica gel plates (F254; 0.5 and 0.25 mm layers) and silica gel GF uniplates for analytical thin layer chromatography (TLC) were manufactured respectively by E. Merck and Analtech, Inc., Newark, Del. The thin layer chromatograms were viewed by short wavelength UV light and/or developed by anisaldehyde-acetic acid-sulfuric acid (1:97:2) spray reagent folowed by heating at approximately 150° C. for 5–10 minutes.

Ultraviolet spectra were obtained using a Hewlett-Packard 8450 UV/VIS spectrophotometer equipped with a HP-7225A plotter. Optical rotations were measured with a Perkin-Elmer 241 variable wavelength polarimeter. Infrared spectra were recorded using a Nicolet FTIR Model MX-1 instrument. All SP-SIMS mass spectra were obtained using a V.G. Analytical MM ZAB-2F mass spectrometer. For high resolution mass measurements, the sample was dissolved in 2-hydroxyethyl disulfide containing potassium iodide.

The NMR spectra were measured using a Bruker AM-400 narrow bore spectrometer, with an ASPECT 3000 computer and pulse programmer, operating at 400.13 MHz and 100.62 MHz for $^1$H- and $^{13}$C-NMR respectively. Spectra were obtained in deuteriochloroform solution using a Bruker 5-mm $^1$H $^{13}$C dual switchable probehead.

EXAMPLE 2

Gulf of California Bugula neritina(Linnaeus). The 12.5 kg (wet wt) of B. neritina (Bryozoa phylum) recollected in 1982 at Bahia Kino-Sonora, Mexico in January 1982 was identified and initially extracted with 2-propanol followed by 1:1 methylenechloride-methanol as previously summarized. The methylene chloride extracts prepared from the 2-propanol preserving solution gave a 50.9 g fraction and water phase gave a 181.9 g fraction. The corresponding methylene chloride and water fractions prepared from the methylene chloride-methanol (1:1) extracts weighed 21.5 and 80.1 g respectively. Both methylene chloride extracts were significantly active against the P388 lymphocytic leukemia with the former showing T/C 141–168 (6.25–25 mg/kg) and $ED_{50}$ 3.4 μg/mL and the latter T/C 141–170 (6.25–25 mg/kg and $ED_{50}$ 4.8 μg.mL.

Both methylene chloride fractions were combined, dissolved in 9:1 methanol-water and extracted with hexane. The methanol-water solution was diluted to 4:1 and re-extracted with carbon tetrachloride. The resulting hexane (38.4 g), carbon tetrachloride (14.5 g) and 4:1 methanol-water (13.6 g) fractions were subjected to biological evaluation and the carbon tetrachloride fraction was found to contain the concentrated PS active (T/C 155–161 at 3 mg/kg, and $ED_{50}$ 2.0 μg/mL) constituents.

EXAMPLE 3

Isolation of Bryostatin 9. Bryostatin 9 was isolated as colorless needles, melting at 159°–162° C., $[\alpha]_D^{28}$ +87.31 (c=0.4, $CH_3OH$), $uv_{max}^\lambda$ ($CH_3OH$) 229 nm (36,200) $ir_{max}^\nu$ (KBr) 3465, 3440, 2975–2940, 1735, 1725, 1655–1645, 1440, 1380, 1365, 1290, 1240, 1160, 1100, 1080, 1070, 1045, 1000 and 870 cm$^{-1}$, sp-sims: m/z 875 [M+Na]+, 875 [M+Na−18]+, 843 [M+Na−32]+, 833 [M+Na−42]+, 817 [M+Na−58]+, 815 [M+Na−60]+, and 787 [M+Na−88]+.

Acetylation of Bryostatin 9. Bryostatin 9 (1.2 mg) was acetylated with acetic anhydride (0.1 mL) and pyridine (0.15 mL) for 4 hours at room temperature. The mixture was concentrated under $N_2$ gas and dried. The hplc reversed phase column (C-18) chromatography of the crude product with methanol-water mixture (from 50:50 to 90:10) gave 0.7 mg of the acetate, from methylene chloride-methanol mixture, as colorless needles, melting at 155°–192° C., $[\alpha]_D^{27}$+95.70 (c=0.05, $CH_3OH$), $uv_{max}^\lambda$ ($CH_3OH$) 228 nm (ε35,500) $ir_{max}^\nu$ (KBr) 3465, 2980–2950, 1740, 1725, 1655–1640, 1438, 1375, 1365, 1285, 1240, 1160, 1100, 1085, 1070, 1048, 1000 and 875 cm$^{-1}$, sp-sims: m/z 917 [M+NA]+, (M+894 for $C_{45}H_{66}O_8$), 899 [M+Na−18]+, 885 [M+Na−32]+, 875 [M+Na−42]+, 873 [M+Na−44]+, 871 [M+Na−46]+, 859 [M+Na−58]+, 857 [M+Na−60]+, 829 [M+Na−88]+, tlc: Rf 0.31 [Rf of Bryostatin 6 acetate: 0.37 with n-hexane-acetone (7:3, silica gel).

EXAMPLE 4

Isolation of Bryostatins 10 and 11. A solution of the carbon tetrachloride fraction (14.5 g) prepared from B. neritina in methylene chloride was chromatographed on a dry column (3.8×100 cm) of silica gel using a gradient of 99:1 to 1:1 methylene chloride-methanol. A 0.291 g fraction with PS T/C 130–158 at 200–800 μg/kg and $ED_{50}$ 1.1×10$^{-3}$ μg/mL was selected for detailed separation guided by PS bioassay and thin layer chromatography using 90:10:0.8 methylene chloride-methanol-water on silica gel. After spraying with the anisaldehyde-acetic acid reagent and heating the bryostatins appear as reddish-purple coloration.

The following procedure was found most effective for separating Bryostatins 9, 10 and 11 from the above fraction. The 0.291 g PS active fraction was carefully separated by a preparative high performance liquid chromatographic sequence using first reversed phase with a 1:1–9:1 methanol-water gradient followed by normal phase with 150:350:3:0.3 ethyl acetate-heptane-methanol-water. The active fraction (74 mg) containing bryostatins 10 and 11 was obtained as a multicomponent (by TLC with 7:3 hexane-acetone and 4:6 hexane-ethyl acetate) amorphous powder. The new bryostatins were further concentrated using silica gel column chromatography in a sequence of separations starting with a gradient of 5:1→1:1 hexane-acetone and lastly with a silica gel column utilizing a 3:1→1:2 hexane-ethyl acetate gradient. In each case a dry column (1.0×60 cm) column technique was performed. Final separation and purification of bryostatins 10 and 11 was realized with reversed phase HPLC with a 1:1→9:1 gradient of methanol-water and a flow rate of 2.0 mL/min. The same procedure was used for final purification of each component. By this means, bryostatin 4 (12.3 mg), bryostatin 5 (3.0 mg), bryostatin 6 (2.8 mg), bryostatin 7 (0.6 mg), bryostatin 8 (0.5 mg), bryostatin 10 (9.2 mg, $8 \times 10^{-7}\%$ yield), and bryostatin 11 and 9 as a difficultly separable mixture (2.0 mg) was obtained. Eventually application of this separation procedure to 50 kg (wet wt) of *B. neritina* from the Gulf of Mexico allowed us to isolate 33.4 mg ($7 \times 10^{-7}\%$ yield) of bryostatin 10 and 8.1 mg ($2 \times 10^{-7}\%$ yield) of bryostatin 11 in pure form (see below).

EXAMPLE 5

Bryostatin 10. An analytical specimen of Bryostatin 10 crystallized from methylene chloride-methanol as plates melting at 161°–164°; silica gel TLC Rf 0.41 (7:3 hexane-acetone), 0.58 (1:1 hexane-ethyl acetate) and 0.27 (reversed phase 4:1 methanol-water); MS (SP-SIMS) M+ 808 $C_{42}H_{64}O_{15}$, with sodium iodide in sulfolane, (m/z) 831.4134 ([M+Na]+, calcd for $C_{42}H_{64}O_{15}Na$: 831.4143), 813 [M+Na−18]+, 799 [M+Na−32]+, 773 [M+Na−58]+, 741 [M+Na−90]+ and 729 [M+Na−102]+, with silver tetrafluoroborate in sulfolane, 915 and 917 [M+Ag$^{107}$ and M+Ag$^{109}$]+, 897 and 899 [M+Ag isotopes−18]+, and 879, 881 [M+Ag isotopes−36]+; $[\alpha]_D^{27}+99.8°$ (c 0.04, $CH_3OH$); UV ($CH_3OH$)$\lambda_{max}$ 229 (ε36,200); IR (KBr) 3470, 2980–2945, 1720, 1650, 1645, 1435, 1380, 1370, 1285, 1230, 1150, 1100, 1075, 1060, 1000, and 860 cm$^{-1}$. The $^{13}C$ NMR data is shown on the structure for Bryostatin 10, supra, and the 400 MHz spectral assignments have been recorded in Table A shown below in Example 6.

Due to the very valuable nature of Bryostatins 10 and 11, and the fact that the mass and nuclear magnetic resonance spectral data provided unequivocal support for the structural assignments, elemental analyses were not pursued.

EXAMPLE 6

Bryostatin 11. A pure sample of Bryostatin 11 crystallized from methylene chloride-methanol as needles melting at 171°–173°: TLC Rf 0.31 on a reversed phase plate with 4:1 methanol-water; MS (SP-SIMS) mol wt 766 for $C_{39}H_{58}O_{15}$ using sodium iodide in sulfolane, (m/z) 789.3675([M+Na]+, calcd for $C_{39}H_{58}O_{15}Na$: 789.3672), 771 [M+Na−18]+, 757 [M+Na−32]+, 731 [M+Na−58]+, 729 [M+Na−60]+ and 699 [M+Na−90]+; $[\alpha]_D^{27}+42.5°$ (c 0.05, $CH_3OH$); UV$\lambda_{max}CH_3OH$ 227 (ε35,500)) nm; and IR (KRr) 3465, 2980–2945, 1740, 1720, 1658–1640, 1440, 1380, 1365, 1280, 1240, 1160, 1095, 1075, 1040, 1000, and 875 cm$^{-1}$. The quantity of Bryostatin 11 was not sufficient for $^{13}$C-NMR determinations, but was very effective for the 400 $^1$H-NMR spectra summarized in Table A below.

TABLE A

Bryostatins 10 and 11 $^1$H NMR (400 MHz) Chemical Shift Assignments (Relative to Tetramethylsilane) in Deuteriochloroform Solution

| Structure 3 Assignment No. | Bryostatin 10 | Multiplicity (J, Hz) | Bryostatin 11 | Multiplicity (J, Hz) |
|---|---|---|---|---|
| 2 | 2.45 | m | 2.449 | m |
| 3 | 4.15 | m | 4.148 | m |
| 4 | 1.60, 2.05 | m,m | 1.60, 2.05 | m,m |
| 5 | 4.18 | m | 4.192 | m |
| 6 | 1.42, 1.74 | m,m | 1.42, 1.75 | m,m |
| 7 | 5.09 | m | 5.048 | m |
| 10 | 1.66, 2.16 | m,m | 1.67, 2.16 | m,m |
| 11 | 3.87 | m | 3.863 | m |
| 12 | 2.18 | m | 2.185 | m |
| 14 | 1.85, 2.05 | m,m | 1.85, 2.05 | m,m |
| 15 | 4.10 | m | 4.065 | m |
| 16 | 5.421 | dd(8.4, 15.8) | 5.329 | dd(846, 15.78) |
| 17 | 5.799 | d(15.8) | 5.798 | d(15.78) |
| 20 | 2.441 | d(10.5) | 2.443 | d(10.5) |
| 22 | 1.85, 2.00 | m,m | 1.85, 2.00 | m,m |
| 23 | 3.98 | m | 3.964 | m |
| 24 | 1.78, 1.90 | m,m | 1.77, 1.95 | m,m |
| 25 | 5.04 | m | 5.111 | m |
| 26 | 3.74 | m | 3.807 | m |
| 27 | 1.200 | d(6.3) | 1.203 | d(6.3) |
| 28* | 1.062 | s | 1.062 | s |
| 29* | 1.005 | s | 1.002 | s |
| 30 | 5.663 | s | 5.667 | s |
| 32* | 1.005 | s | 0.992 | s |
| 33* | 0.924 | s | 0.929 | s |
| 34 | 5.677 | s | 5.676 | s |
| 36 | 3.688 | s | 3.688 | s |
| 37 | 3.649 | s | 3.649 | s |
| C-7 Isovalerate | | | C-7 Acetate | |
| 2' | 2.23 | m | 2.027 | s |
| 3' | 1.85–1.95 | m | | |
| 4' | 1.17 | d(14.5) | | |
| 5' | | | | |

*Assignments for these four groups may be interchanged

EXAMPLE 7

Acid-Catalyzed Hyrolysis of Bryostatin 10. Method A. A solution of Bryostatin 10 (1.2 mg) in 0.2 mL of methanol containing 1% hydrochloric acid was allowed to remain at room temperature for 3 days. The solvent was concentrated under a stream of nitrogen and the crude product (1.0 mg) was chromatographed by reversed phase HPLC on a C-18 column using a gradient of 1:1 to 9:1 methanol-water. The pure $\Delta^{19}$ (20)-olefin (0.32 mg) derivative of Bryostatin 10 was characterized as described in method C below.

Method B. A solution of Bryostatin 10, 0.2 mg (in methylene chloride-methanol) 0.2 mL of 4:1 was stored at room temperature for one week. By this means 50 μg of the $\Delta^{19}$ (20)-olefin was obtained and identified as noted in method C.

Method C. To a solution of Bryostatin 10, 1.0 mg (in methylene chloride (0.4 mL) was added one drop of 1% hydrochloric acid in methylene chloride. After 30 min the mixture was poured into ice-water and extracted with methylene chloride. The solvent was washed with water, dried and concentrated to dryness. Application of the reversed phase HPLC technique led to 0.41 mg of the $\Delta^{19}$ (20)-olefin derivative of Bryostatin 10 as plates from methylene chloride-methanol: mp 143°–145°; TLC Rf on silica gel 0.33 (7:3 hexane-acetone) and 0.25 (1:1 hexane-ethyl acetate); MS (SP-SIMS) mol wt 790 for $C_{42}H_{62}O_{14}$ from sodium iodide in sulfolane which showed m/z 813 [M+Na]+, 795 [M+Na−18]+, 741 [M+Na−72]+, 723 [M+Na−90]+ and 711 [M+Na−102]+; $[\alpha]_D^{27}$+96.52° (c 0.04, $CH_3OH$); UV$\lambda_{max}$ $CH_3OH$ 226 ($\epsilon$30,500) and 301 ($\epsilon$36,900) nm; IR (KBr) 3465, 2980–2940, 1725, 1600, 1650, 1645, 1570, 1440, 1380, 1370, 1285, 1230, 1150, 1100, 1075, 1060, 1000, and 870 cm$^{-1}$; and 400 MHz $^1$H-NMR (in deuterio-chloroform in respect to tetramethylsilane) $\delta$ 0.98 and 1.049 (s, C−28 and 29H), 1.17 (d, J=14.5, side-chain dimethyl), 1.211 (d, J=6.3 Hz, C−27H), 1.232 (s, C−32 and 33H), 2.17 (m, C−12H), 2.45 (m, C−2H), 3.667 (s, C−36), 3.697 (s, C−37H), 5.217 (s, C−20H), 5.412 (dd, J=8.3 Hz and 15.56 Hz, C−16H), 5.600 (s, C−30H), and 6.010 (d, J=15.56 Hz, C−17H).

EXAMPLE 8

Bryostatin 10, 26-Acetate. A 2.8 mg sample of Bryostatin 10 was acetylated and purified in acetic anhydride (0.4 mL)-pyridine (0.20 mL) at room temperature during 4 hours. Upon mixture with ice-water it was extracted with methylene chloride. The chlorocarbon solution was washed with dilute hydrochloric acid, water, dried and solvent removed. The crude product was purified by HPLC chromatography on a C-18 reversed phase column (9.4 mm ID×500 mm) using a 1:1→9:1 gradient of methanol-water. By this preparative HPLC procedure, a pure specimen (8.0 mg) of Bryostatin 10, 26-acetate was obtained. Recrystallization from methylene chloride-methanol gave plates melting at 145°–148°; TLC Rf on silica gel 0.52 (7:3 acetone-hexane) and 0.73 (1:1 hexane-ethyl acetate); mol wt 850 for $C_{44}H_{66}O_{16}$ from sodium iodide in sulfolane where m/z found was 873 [M+Na]+, 855 [M+Na−18]+, 841 [M+Na−32]+, 813 [M+Na−60]+, 783 [M+Na−90]+ and 771 [M+Na−102]+; $[\alpha]_D^{27}$+56.85 (c 0.035, $CH_3OH$); UV$\lambda_{max}$ $CH_3OH$ 228 ($\epsilon$36,000) nm; IR (KBr) 3450, 2980–2945, 1740, 1725, 1650, 1645, 1435, 1375, 1360, 1285, 1230, 1150, 1100, 1080, 1060, 100 and 860 cm$^{-1}$; and the $^1$H-NMR (400 MHz) summarized in Table B, below.

TABLE B

Bryostatin Acetate $^1$H NMR (400 MHz) Chemical Shift Assignments (Relative to Tetramethylsilane) in Deuteriochloroform Solution

| Structure Assignment No. | Bryostatin 10 Acetate | |
|---|---|---|
| | $\delta$ | Multiplicity (J, Hz) |
| 2 | 2.462 | m |
| 3 | 4.149 | m |
| 4 | 1.60, 2.05 | m,m |
| 5 | 4.179 | m |
| 6 | 1.42, 1.74 | m,m |
| 7 | 5.069 | m |
| 10 | 1.66, 2.16 | m,m |
| 11 | 3.849 | m |
| 12 | 2.18 | m |
| 14 | 1.85, 2.05 | m,m |
| 15 | 4.124 | m |
| 16 | 5.323 | dd(8.4, 15.7) |
| 17 | 5.811 | d(15.7) |
| 20 | 2.437 | d(10.3) |
| 22 | 1.85, 2.00 | m,m |
| 23 | 3.919 | m |

TABLE B-continued

Bryostatin Acetate $^1$H NMR (400 MHz) Chemical Shift Assignments (Relative to Tetramethylsilane) in Deuteriochloroform Solution

| Structure Assignment No. | Bryostatin 10 Acetate | |
|---|---|---|
| | $\delta$ | Multiplicity (J, Hz) |
| 24 | 1.78, 1.90 | m,m |
| 25 | 5.294 | m |
| 26 | 5.036 | m |
| 27 | 1.243 | d(5.9) |
| 28* | 1.056 | s |
| 29* | 1.004 | s |
| 30 | 5.664 | s |
| 32* | 1.004 | s |
| 33* | 0.927 | s |
| 34 | 5.677 | s |
| 36 | 3.692 | s |
| 37 | 3.650 | s |
| C-7 Isovalerate | | |
| 2' | 2.23 | m |
| 3' | 1.85–1.95 | m |
| 4' | 1.174 | d(14.5) |
| 5' | | |
| C-20 Butyrate | | |
| 26-OCOCH$_3$ | 2.055 | s |

*Assignments for these four positions may be interchanged

EXAMPLE 9

Bryostatin 10 26-m-bromobenzoate. The esterification of Bryostatin 10 (2.3 mg) with m-bromobenzoyl chloride (0.44 mL) in pyridine (0.50 mL) and isolation of product was conducted as described above for obtaining m-bromobenzoate. A pure sample of 26-m-bromobenzoate (1.84 mg, 80% yield) recrystallized from methylene chloride-methanol as plates: mp 164°–168°; MS (SP-SIMS) mol wt 991 for $C_{49}H_{67}BrO_{16}$ from m/z 1014 [M+Na]+, 996 [M+Na−18]+, and 956 [M+Na−58]+; $[\alpha]_D^{27}$+77.4 (c 0.035, $CH_3OH$); UV$\lambda_{max}$ $CH_3OH$ 229 ($\epsilon$36,200) and 265 ($\epsilon$6,800) nm and IR (KBr) 2445, 2980–2950, 1740, 1728, 1658–1640, 1440, 1380, 1365, 1280, 1245, 1160, 1100, 1090, 1085, 1050, 1000, and 875 cm$^{-1}$. The high resolution (400 MHz) proton NMR spectrum was as expected for Bryostatin 10 26m-bromobenzoate 2c.

EXAMPLE 10

26-oxo-Bryostatin 10. The oxidation of Bryostatin 10, 3.0 mg (with chromium trioxide, 1.2 mg) in pyridine (1.2 mL) and purification of product was executed as summarized for obtaining 26-oxo-bryostatin 4. Recrystallization from methylene chloride-methanol gave pure plates (1.8 mg, 60% yield) of 26-oxo-bryostatin 10; mp 163°–165°; MS (SP-SIMS) mol wt 860 for $C_{42}H_{62}O_{15}$ from m/z 829 [M+Na]+, 817 [M+Na−18]+, 771 [M+Na−58]+, 739 [M+Na−90]+, 727 [M+Na−102]+; $[\alpha]_D^{27}$+95.2° (c 0.035, $CH_3OH$); UV$\lambda_{max}$ $CH_3OH$ 227 ($\epsilon$36,050) nm; IR (KBr) 3450, 2980–2938, 1745, 1724, 1650, 1435, 1370, 1360, 1285, 1240, 1165, 1100, 1085, 1045, 1025, 1000 and 870 cm$^{-1}$. The high resolution proton NMR spectrum and interpretation has been summarized in Table C, below.

TABLE C 26-oxo-Bryostatin 10 $^1$H NMR (400 MHz) Chemical Shift Assignments (Relative to Tetramethylsilane) in Deuteriochloroform Solution

| Structure Assignment No. | 26-oxo-Bryostatin 10 | |
|---|---|---|
| | δ | Multiplicity (J, Hz) |
| 2 | 2.539 | m |
| 3 | 4.188 | m |
| 4 | 1.585, 2.097 | m,m |
| 5 | 4.179 | m |
| 6 | 1.419, 1.764 | m,m |
| 7 | 4.903 | m |
| 10 | 1.576, 2.109 | m,m |
| 11 | 3.866 | m |
| 12 | 2.203 | m |
| 14 | 1.877, 2.115 | m,m |
| 15 | 4.055 | m |
| 16 | 5.349 | dd(8.33, 15.67) |
| 17 | 5.694 | d(15.67) |
| 20 | 2.399 | d(10.6) |
| 22 | 1.800, 2.203 | m,m |
| 23 | 4.255 | m |
| 24 | 1.768, 2.139 | m,m |
| 25 | 5.113 | m |
| 26 | — | |
| 27** | 2.187 | s |
| 28* | 1.081 | s |
| 29* | 1.016 | s |
| 30 | 5.662 | s |
| 32* | 1.010 | s |
| 33* | 0.925 | s |
| 34 | 5.707 | s |
| 36 | 3.683 | s |
| 37 | 3.652 | s |
| 2' | 2.25 | m |
| 3' | 1.95–2.00 | m |
| 4' | 1.17 | d(14.5) |
| 5' | | |

*Assignments for these four positions may be interchanged
**The 27-methyl signal of 26-oxo-Bryostatin 4 appears at 2.153 ppm as a sharp singlet.

EXAMPLE 11

13→30-epoxy Bryostatin 10. The epoxidation of Bryostatin 10 (3.0 mg) was pursued and the epoxide of Bryostatin 10 isolated in 63% yield (1.9 mg) by adding 1.5 mg of m-chloroperbenzoic acid to a solution of the Bryostatin 10 in methylene chloride (0.5 mL) and holding the mixture at room temperature for 48 hours. Upon dilution with ice water and extraction with methylene chloride, the solution was washed with aqueous sodium bisulfite and potassium iodide followed by water. After removal of the solvent, the crude product was purified by the HPL chromatographic of Example B. Recrystallization from methylene chloride-methanol provided 2.0 mg of the 13-30 epoxide as plates melting at 184°–186°; MS (SP-SIMS) mol wt 824 for $C_{42}H_{64}O_{16}$ from m/z 847 [M+Na]+, 829 [M+Na−18]+, 815 [M+Na−32]+, 789 [M+Na−58]+, 757 [M+Na−90]+ and 745 [M+Na−102]+; $[\alpha]_D^{27}$+88.5° (c 0.035, $CH_3OH$); UV$\lambda_{max}$ (ε36,000) nm; IR (KBr) 3460, 2980–2940, 1740, 1720, 1650, 1435, 1380, 1358, 1283, 1235, 1165, 1100, 1080, 1030, 1000, and 872 cm$^{-1}$. A summary of the proton NMR spectrum with assignments has been presented in Table D, below.

TABLE D

Bryostatin Epoxide $^1$H NMR (400 MHz) Chemical Shift Assignments (Relative to Tetramethylsilane) in Deuteriochloroform Solution

| Structure Assignment No. | Bryostatin 10 Epoxide | |
|---|---|---|
| | δ | Multiplicity (J, Hz) |
| 2 | 2.576 | m |
| 3 | 4.155 | m |
| 4 | 1.80, 2.05 | m,m |
| 5 | 4.257 | m |
| 6 | 1.42, 1.66 | m,m |
| 7 | 5.104 | m |
| 10 | 1.48, 1.85 | m,m |
| 11 | 4.120 | m |
| 12 | 2.00 | m |
| 14 | 1.55, 1.80 | m,m |
| 15 | 4.399 | m |
| 16 | 5.220 | dd(8.3, 15.8) |
| 17 | 5.824 | d(15.8) |
| 20 | 2.442 | d(10.2) |
| 22 | 1.78, 2.05 | m,m |
| 23 | 4.002 | m |
| 24 | 1.75, 1.98 | m,m |
| 25 | 5.160 | m |
| 26 | 3.740 | m |
| 27 | 1.210 | d(6.3) |
| 28* | 1.108 | s |
| 29* | 0.993 | s |
| 30 | 3.359 | s |
| 32* | 0.984 | s |
| 33* | 0.903 | s |
| 34 | 5.685 | s |
| 36 | 3.760 | s |
| 37 | 3.652 | s |
| C-7 Isovalerate | | |
| 2' | 2.25 | m |
| 3' | 1.95–2.00 | m |
| 4' | 1.17 | d(14.5) |
| 5' | | |

*Assignments for these four positions may be interchanged

EXAMPLE 12

The chromatographic and instrumental techniques employed in the following examples are descibed in G. R. Pettit et al, J. Am. Chem. Soc, 106, 6768 (1984) which also describes animal taxonomy and recollection data techniques. In each case, Bugula veritina from a Gulf of Mexico recollection was used as the starting material. The initial methylene chloride fraction from a methylene chloride-methanol extraction procedure was subjected to a 9:1 4:1 methanol-water solvent partitioning sequence with hexane carbon tetrachloride. The latter chlorocarbon fraction was extensively separated (PS bioassay guidance) as described in G. R. Pettit et al, Tetrahedron, 41 985, 1985, using gel permeation and partition chromatography on Sephadex LH-20, silica gel, and reversed phase column chromatography, preparative layer and high perfomance liquid chromatography.

EXAMPLE 13

Hydrolysis of Bryostatin 9. A 1.0 mg sample of Bryostatin 9 was hydrolyzed for three days at 18°–20° C. in 0.4 mL of 1% hydrochloric acid in methanol. The mixture was concentrated under $N_2$ gas and dried. By hplc reversed phase column (C-18) chromatography using methanol-water mixture, the hydrolysis product was isolated in 0.65 mg yield. The compound was obtained as a colorless powder, melting at 147°–149° C. $[\alpha]_D^{26}$+87.24 (c=0.03, $CH_3OH$), uv$\lambda_{max}$ 229 nm (ε36,100) ir $\nu_{max}$ (KBr) 3470, 2980–2950, 1742, 1725, 1658–1640, 1435, 1380, 1370, 1288, 1240, 1160, 1100, 1090, 1075, 1050, 1000 and 870 cm$^{-1}$, sp-sims: m/z 833 [M+Na]$^+$, (M+180 for $C_{41}H_{62}O_{16}$), 815 [M+Na−18]$^+$, 775 [M+Na−58]$^+$, 745 [M+Na−88]$^+$, tlc: Rf 0.45 on a reversed phase tlc plate with methanol-water (4:1). The degradation product gave the same physical properties as found for the hydrolysis product obtained for Bryostatin 8 (See: Pettit, G. R. et al, Tetrahedron, 41, 985 1985).

EXAMPLE 14

*Bugula neritina* (Linnaeus). In 1981, 4000 liters corresponding to 1,000 kg damp wt. of the marine sea mat *Bugula neritina* (Bryozoan phylum) was collected near Monterey, California and preserved in 2-propanol for 30 months.

Animal extraction: The 2-propanol was removed from the 4,000 liter recollection of *Bugula neritina* and the semi-dry animal (approximately 1,000 kg) was re-extracted with 2-propanol (91%) for two weeks. The combined 2-propanol extracts were concentrated to 190 liters, placed in a 1000 L stainless steel vessel, and partitioned (5x) between 180 L volumes each of distilled water and methylene chloride. After concentration the methylene chloride extract (16.4 kg) was partitioned between hexane (4×100 L) and methanol-water (9:1). The hexane phase was separated and the methanol-water portion was evaporated to dryness to afford 1.8 kg of solid. The 1.8 kg residue was chromatographed on a series of 15×305 cm stainless steel HPLC columns prepared from 61 kg of Davisil 633 grade Silica Gel (200–400 mesh) in methylene chloride. Elution was begun with methylene chloride followed by an increasing methanol gradient. The flow rate was approximately 68 L/hr. Fractions measuring 20 L were collected and combined on the basis of TLC (4–7% methanol in methylene chloride), giving twenty-six major fractions.

EXAMPLE 15

Isolation of Bryostatin 12 and 13: Analytical TLC of adjacent fractions from the purification of Bryostatins 1 and 2, using 7:3 hexane-acetone and 3:2 ethyl acetate-hexane, revealed the possible presence of other bryostatin-type constituents in relatively minor amounts. Such fractions were individually chromatographed employing RP-18 reversed phase HPLC. In each case, elution was begun with methanol-water (1:1) at a flow rate of 2.0 mL/min with a gradient to methanol. By this means pure specimens of amorphous Bryostatin 3 (1.6 mg), Bryostatin 8 (13.2 mg), Bryostatin 9 (16.4 mg), Bryostatin 12 (3.7 mg), and Bryostatin 13 (0.7 mg) were isolated. Known Bryostatins 1, 2, 3, and 8 were identified by direct comparison (principally by 400 MHz NMR, SP-SIMS molecular wt. determinations) with authentic samples and by co-TLC in several solvent systems.

Bryostatin 12: $C_{49}H_{72}O_{17}$; TLC Rf 0.56 ($CH_2Cl_2$—$CH_3OH$ 95:5); MS (SP-SIMS) m/z 971 [M+K]$^+$; 957 [M+K—$CH_3$+H]$^+$, 897 [M+K—$COCH_2CH_2CH_3$—3H]$^+$, and 883 [M+K—O-$COCH_2CH_2CH_3$—H]$^+$; $[\alpha]_D^{27}$+39 (c 0.108, $CH_3OH$); UV$\lambda_{max}$ ($CH_3OH$) 231 and 263 nm (log ε4.46, 4.47); IR$\nu_{max}$ (thin film on NaCl) 3470, 3346, 2964–2949, 1734, 1717, 1660–1640, 1440, 1380, 1365, 1270, 1250, 1220, 1164, 1100, 1070, 1055, 1000 and 860 cm$^{-1}$. The $^{13}$C-NMR data is shown on the structure diagram Bryostatin 12, supra.

Bryostatin 13: $C_{41}H_{62}O_{15}$; TLC Rf 0.51 ($CH_2Cl_2$—$CH_3OH$ 95:5); MS (SP-SIMS) m/z 833 [M+Na]$^+$, low resolution MS m/z 817 [M+Na]$^+$, 745 [M+Na—$COCH_2CH_2CH_3$—H]$^+$, and 727 [M+Na—$OCOCH_2CH_2CH_3$—3H]$^+$; UV$\lambda_{max}$ ($CH_3OH$) 228 nm (log ε3.96); IR$\nu_{max}$ (thin film) 3475, 3359, 2926, 1734, 1717, 1685, 1653, 1606, 1436, 1380, 1153, 1096 and 1077 cm$^{-1}$. The $^1$H-NMR data is shown on the structure diagram of Bryostatin 13, supra.

EXAMPLE 16

Conversion of Bryostatin 2 to Bryostatin 12. A 20 mg sample of Bryostatin 2 was treated with pyridine (0.25 mL and butyric acid anhydride (0.5 mL). The solution was allowed to stand for 44 hours at room temperature (under nitrogen) and concentrated to dryness. Preparative TLC using 7:3 hexane-acetone led to 12 mg of Bryostatin 2 dibutyrate ($C_{53}H_{78}O_{18}$) TLC Rf 0.80 ($CH_2Cl_2$—MeOH 95:5) and MS (SP-SIMS) m/z 1041 [M+K]$^+$.

To a solution of Bryostatin 2 dibutyrate (12 mg) in ethanol (1 mL) was added 6.0N hydrochloric acid (0.25 mL). After removal of the ethanol, the residue was partitioned between methylene chloride and water. The chlorocarbon phase was dried over anhydrous sodium sulfate, the solvent evaporated and the residue purified by preparative TLC using 95:5 methylene chloride-methanol as the mobile phase to afford 2.5 mg of Bryostatin 12 identical (by comparison TLC and $^1$H-NMR, $^{13}$C-NMR, IR, UV, $[\alpha]_D$ and SP-SIMS spectral properties) with the natural product. Recovered starting material was resubmitted to the same hydrolysis procedure to improve the yield of Bryostatin 12.

The administration of Bryostatins 9–13 is useful for treating animals or humans bearing a neoplastic disease, for example, acute myelocytic leukemia, acute lymphocytic leukemia, malignant melanoma, adenocarcinoma of lung, neuroblastoma, small cell carcinoma of lung, breast carcinoma, colon carcinoma, ovarian carcinoma, bladder carcinoma, and the like.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; intraperitoneal, 1 to about 500 mg/kg; subcutaneous, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention for localized use about the cutis, intranasally, pharyngolaryngeally, bronchially, broncholially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as a talc, magnesium sterate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions, the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof.

EXAMPLE 17

Several dosage forms were prepared embodying the present invention. They are shown in the following examples in which the notation "active ingredient" signifies Bryostatin 9, Bryostatin 10, Bryostatin 11, Bryostatin 12, Bryostatin 13, their synthetic counterparts and the non-toxic pharmaceutically active derivatives thereof.

COMPOSITION "A"

Hard-Gelatin Capsules

One thousand two-piece hard gelation capsules for oral use, each capsule containing 200 mg of an active ingredient are prepared from the following types and amounts of ingredients:

| Active ingredient, micronized | 200 gm |
|---|---|
| Corn Starch | 20 gm |
| Talc | 20 gm |
| Magnesium stearate | 2 gm |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing a active ingredient in 50, 250 and 500 mg amounts by substituting 50 gm, 250 gm and 500 gm of a active ingredient for the 200 gm used above.

COMPOSITION "B"

Soft Gelatin Capsules

One-piece soft gelatin capsules for oral use, each containing 200 mg of a active ingredient (finely divided by means of an air micronizer), are prepared by first suspending the compound in 0.5 ml of corn oil to render the material capsulatable and then capsulating in the above manner.

The foregoing capsules are useful for treating a neoplastic disease by the oral administration of one or two capsules one to four times a day.

COMPOSITION "C"

Tablets

One thousand tablets, each containing 200 mg of a active ingredient are prepared from the following types and amounts of ingredients:

| Active ingredient micronized | 200 gm |
|---|---|
| Lactose | 300 gm |
| Corn starch | 50 gm |
| Magnesium stearate | 4 gm |
| Light liquid petrolatum | 5 gm |

The active ingredient finely divided by means of an air micronizer, is added to the other ingredients and then thoroughly mixed and slugged. The slugs are broken down by forcing through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing a active ingredient in 250 mg and 100 mg amounts by substituting 250 gm and 100 gm of a active ingredient for the 200 gm used above.

COMPOSITION "D"

Oral Suspension

One thousand ml of an aqueous suspension for oral use, containing in each teaspoonful (5 ml) dose, 50 mg of a active ingredient, is prepared from the following types and amounts of ingredients:

| Active ingredient micronized | 10 gm |
|---|---|
| Citric acid | 2 gm |
| Benzoic acid | 1 gm |
| Sucrose | 790 gm |
| Tragacanth | 5 gm |
| Lemon Oil | 2 gm |
| Deionized water, q.s. 1000 ml. | |

The citric acid, benzoic acid, sucrose, tragacanth and lemon oil are dispersed in sufficient water to make 850 ml of suspension. The active ingredient finely divided by means of an air micronizer, is stirred into the syrup unitl uniformly distributed. Sufficient water is added to make 1000 ml.

The composition so prepared is useful for treating a neoplastic disease at a dose of 1 tablespoonful (15 ml) three times a day.

COMPOSITION "E"

Parenteral Product

A sterile aqueous suspension for parenteral injection, containing in 1 ml 300 mg of a active ingredient for treating a neoplastic disease, is prepared from the following types and amounts of ingredients:

| Active ingredient, micronized | 30 gm |
|---|---|
| Plysorbate 80 | 5 gm |
| Methylparaben | 2.5 gm |
| Propylparaben | 0.17 gm |
| Water for injection, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1M) three times a day.

COMPOSITION "F"

Suppository, Rectal and Vaginal

One thousand suppositories, each weighing 2.5 gm and containing 200 mg of a active ingredient are prepared from the following types and amounts of ingredients:

| Active ingredient, micronized | 15 gm |
|---|---|
| Propylene glycol | 150 gm |
| Polyethylene glycol #4000, q.s. | 2,500 mg |

The active ingredient is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

COMPOSITION "G"

Intranasal Suspension

One thousand ml of a sterile aqueous suspension for intranasal instillation, containing in each ml 200 mg of a active ingredient, is prepared from the following types and amounts of ingredients:

| | |
|---|---|
| Active ingredient, micronzed | 15 gm |
| Polysorbate 80 | 5 gm |
| Methylparaben | 2.5 gm |
| Propylparaben | 0.17 gm |
| Deionized water, q.s. 1000 ml. | |

All the ingredients, except the active ingredient, are dissolved in the water and the solution sterilized by filtration. To the sterile solution is added the sterilized acitve ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, broncholially or orally.

COMPOSITION "H"

Powder

Five grams of a active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

One hundred grams of a active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

COMPOSITION "J"

Insufflation

One hundred grams of a active ingredient in bulk form is finely divided by means of an air micronizer.

The foregoing composition is useful for treating a neoplastic disease, by the inhalation of 300 mg one to four times per day.

COMPOSITION "K"

Hard Gelatin Capsules

One hundred two-piece hard gelatin capsules were prepared for oral use, each capsule containing 200 mg of an active ingredient. The active ingredient is finely divided by means of an air micronizer and encapsulated in the usual manner. The foregoing capsules are useful for treating a neoplastic disease, by the oral administration of one or two capsules, one to four times a day.

Using the procedure above, capsules are similarly prepared containing active ingredient in 50, 250 and 500 mg amounts by substituting 50 gm, 250 gm and 500 gm of the active ingredient for the 200 gm used above.

From the foregoing, it is apparent that an invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A compound denominated Bryostatin having the general structural formula:

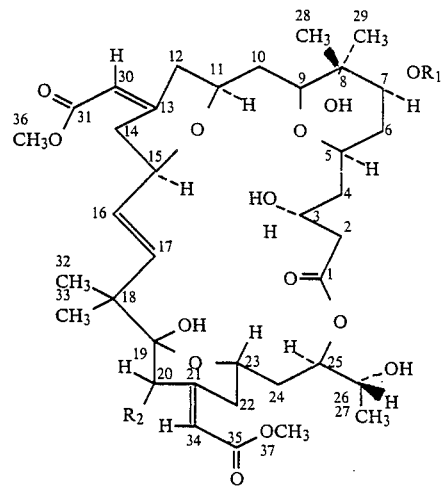

wherein: $R = -COCH_3$; $-COCH_2CH_2CH_3$; or $-COCH_2CH(CH_3)_2$; and $R_2 = H$.

2. A compound according to claim 1 denominated Bryostatin 10 in which $R_1$ is $-COCH_2CH(CH_3)_2$.

3. A compound according to claim 1 denominated Bryostatin 11 in which $R_1$ is $-COCH_3$.

4. A compound according to claim 1 denominated Bryostatin 13 in which $R_1$ is $-COCH_2CH_2CH_3$.

* * * * *